United States Patent [19]
Watanabe et al.

[11] Patent Number: 5,147,610
[45] Date of Patent: Sep. 15, 1992

[54] AUTOMATIC ANALYZING APPARATUS

[75] Inventors: Miyoko Watanabe; Hiroshi Mitsumaki, both of Mito, Japan

[73] Assignee: Hitachi, Ltd., Tokyo, Japan

[21] Appl. No.: 709,881

[22] Filed: Jun. 4, 1991

[30] Foreign Application Priority Data

Jun. 15, 1990 [JP] Japan .................. 2-157263

[51] Int. Cl.$^5$ .................. G01N 33/00; B08B 3/00
[52] U.S. Cl. .................. 422/64; 422/62; 422/63; 422/65; 134/155; 134/166 R
[58] Field of Search .................. 422/2, 3, 28, 62, 63, 422/64, 65, 68.1, 81, 905; 210/756; 134/104.2, 109, 155, 166 R, 169 R, 186

[56] References Cited

U.S. PATENT DOCUMENTS

| | | | |
|---|---|---|---|
| 3,883,305 | 5/1975 | Hoskins et al. | 422/69 X |
| 4,313,735 | 2/1982 | Yamashita et al. | 23/230 R |
| 4,363,783 | 12/1982 | Sitte | 422/63 |
| 4,383,041 | 5/1983 | Kutsusawa et al. | 435/291 |
| 4,855,064 | 8/1989 | Schlein | 210/764 |
| 5,033,492 | 7/1991 | Mertens et al. | 134/166 R |
| 5,066,600 | 11/1991 | Antonevich et al. | 436/52 |

FOREIGN PATENT DOCUMENTS

| | | | |
|---|---|---|---|
| 0140156 | 11/1980 | Japan | 422/64 |
| 0162063 | 12/1980 | Japan | 134/166 R |
| 63-252248 | 10/1988 | Japan | . |
| 2-31165 | 2/1990 | Japan | . |

*Primary Examiner*—Robert J. Warden
*Assistant Examiner*—Christopher Y. Kim
*Attorney, Agent, or Firm*—Fay, Sharpe, Beall, Fagan, Minnich & McKee

[57] ABSTRACT

An automatic analyzing apparatus includes a drainage line for conveying a reaction liquid which has been subjected to an analysis and water used to clean a reaction vessel from the reaction vessel to a waste liquid reservoir. The drainage line includes a vacuum tank, a vacuum pump for sucking a gas separated from a liquid within the vacuum tank and containing suspended particles, and a filter for filtering the gas discharged from the vacuum pump and thereby preventing discharge of an infectious aerosol from the apparatus. The waste liquid reservoir is provided with a sterilizing liquid supply bottle for supplying a sterilizer or a disinfectant into the reservoir.

10 Claims, 3 Drawing Sheets

AUTOMATIC ANALYZING APPARATUS

BACKGROUND OF THE INVENTION

1. Field of the Invention

The present invention relates to an automatic analyzing apparatus and, more particularly, to an automatic analyzing apparatus which is constructed such that it prevents an infectious aerosol generated from an inspected object, such as blood or urine of an organism, or a waste liquid, from injuring health of a human body, such as an operator, during inspection.

2. Description of the Related Art

In the fields of biotechnology and medical inspecting apparatus, there has been growing interest in so-called biohazard in recent years. Hence, there has been an increasing demand for measures against the infection.

To meet such demands, Japanese Patent Un-Examined Publication No. 63-252248 discloses a bacteria analyzing apparatus which includes sterilizing means for sterilizing, by heat or a disinfectant, a liquid sample on which an analysis has been made and a waste liquid made up of a sample spilled from a sample vessel before they are drained from the analyzing apparatus. However, the sterilizing process which employs heat requires a heating device, thus necessitating provision of heat insulation means, such as a heat insulating wall, in the analyzing apparatus complicated. The sterilizing means which uses a sterilizer or the disinfectant includes a sterilizing liquid feeding device for supplying a sterilizing liquid from a bottle thereof to a waste liquid tube. It takes some time for the sterilizing effect of the sterilizing liquid supplied to the waste liquid to be generated. Therefore, any reliable sterilization of the waste liquid drained from the analyzing apparatus through the waste liquid tube cannot be assured.

Japanese Patent Un-Examined Publication No. 2-31165 discloses an automatic analyzing apparatus which includes a filter for removing airborne particles (particularly, infectious aerosol containing microorganism) generated in a housing when a liquid sample is discharged from a probe to a reaction vessel within the housing and thereby preventing discharge of the airborne particles from the analyzing apparatus. Such filter is one of the effective means for preventing environmental contamination by the infectious aerosol. However, the filter cannot fulfill all the requirements for the apparatus. That is, the analyzing apparatus is provided with a vacuum pump to discharge the waste liquid from the reaction vessel after an analysis as well as the water used to clean reaction vessel to the outside of the apparatus. This vacuum pump discharges not only the waste liquid and the cleaning water but also infectious aerosol present in the vicinity of the reaction vessels.

SUMMARY OF THE INVENTION

Accordingly, an object of the present invention is to provide an automatic analyzing apparatus which includes a sterilizing device operable with an agent for the sterilization (sterilizers or disinfectants) to reliably sterilize a waste liquid generated by analysis before the waste liquid is drained from the apparatus.

Another object of the present invention is to provide an automatic analyzing apparatus which includes means for sterilizing an infectious aerosol sucked by a vacuum pump for discharging a waste liquid generated by the analysis and a cleaning water before the aerosol is discharged from the apparatus.

To this end, the present invention provides an automatic analyzing apparatus which comprises: a housing; analysis means including a reaction vessel supporting means disposed within the housing for supporting at least one reaction vessel for accommodating a sample and a reagent, and measurement means for measuring the result of the reaction between the sample and the reagent in the reaction vessel; waste liquid reservoir means detachably disposed in the housing; cleaning means for cleaning by cleaning water a reaction vessel which has been used for analysis; liquid conveying means for conveying the reaction solution formed by the sample and the reagent and the water used for cleaning the reaction vessel to the waste liquid reservoir means; and liquid supply means for supplying a sterilizing liquid, such as a sterilizer or a disinfectant, into the waste liquid reservoir means. The liquid conveying means includes at least one suction nozzle movable into and out of the reaction vessel, a drainage line extending from the nozzle to the waste liquid reservoir means, gas-liquid separation means provided in the drainage line, a vacuum pump for sucking the gas separated from the liquid within the gas-liquid separation means, and a filter disposed on a discharge side of the vacuum pump.

In the automatic analyzing apparatus according to the present invention, since the sterilizing liquid supply means is operative to supply a sterilizer or a disinfectant into the waste liquid reservoir, the waste liquid in the waste liquid reservoir is reliably sterilized and then discharged from the reservoir. Furthermore, as the filter traps the pathogenic airborne particles in the gas separated from the liquid within the drainage line, only the substantially completely cleaned air is discharged from the apparatus to the atmosphere. Therefore, the automatic analyzing apparatus according to the present invention is capable of effectively solving the problems involving the environmental contamination by the infectious aerosol.

Other objects and advantages of the present invention will become more apparent from the following description with reference to the accompanying drawings.

DETAILED DESCRIPTION OF THE PREFERRED EMBODIMENT

Figure 1:
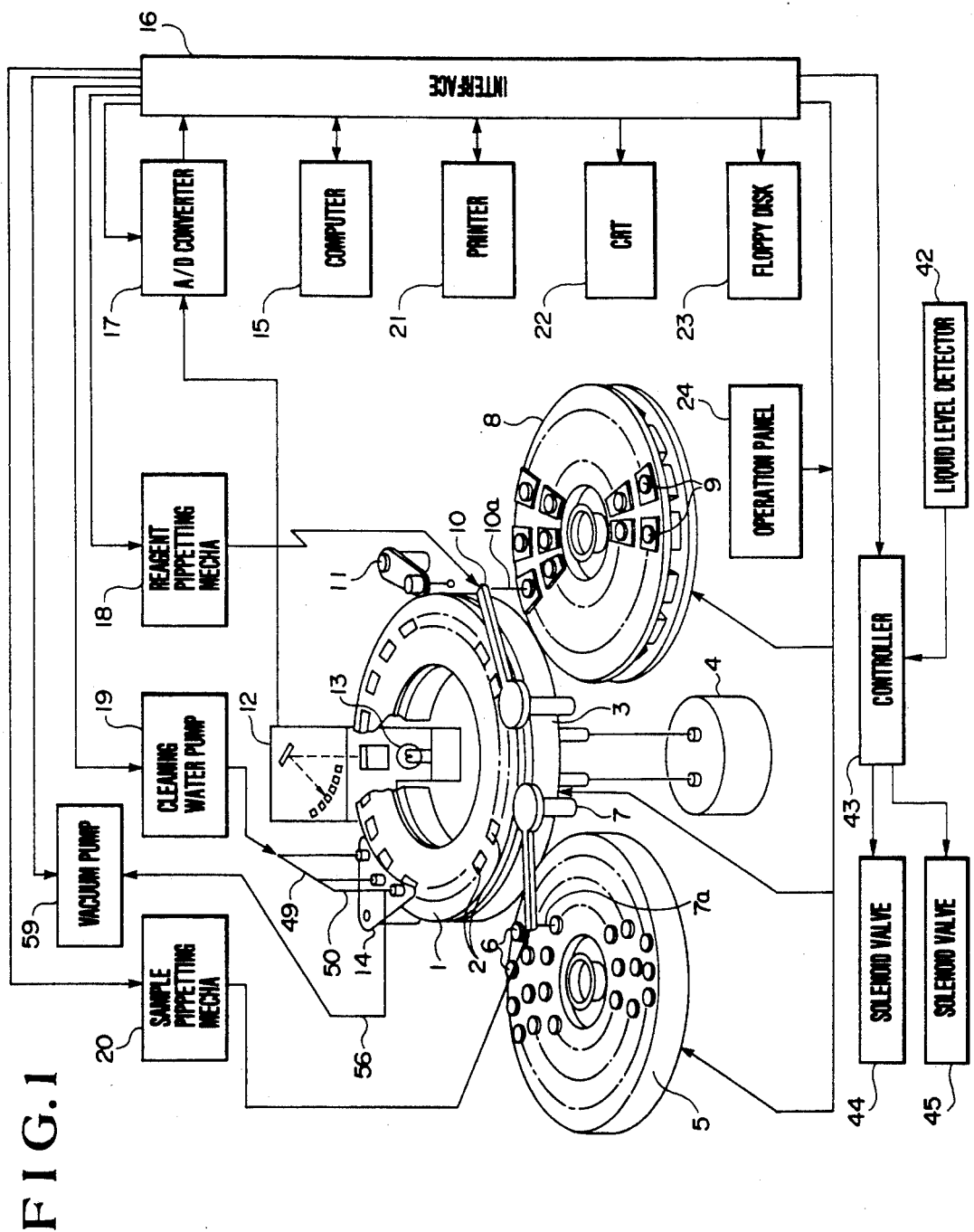
FIG. 1 is a schematic view of an analyzing portion and a control system of an embodiment of an automatic analyzing apparatus according to the present invention.

In an analyzing apparatus shown in FIG. 1, a reaction disk 1 for supporting a large number of reaction vessels 2 on an upper surface thereof is mounted on a frame (not shown) in such a manner as to be rotatable about a vertical axis by a known driving mechanism (not shown). A cylindrical incubation bath 3 is coupled to the under surface of the disk 1 so as to maintain the temperature of the reaction disk 1 at a predetermined level. In the incubation bath 3, a fluid having a predetermined temperature is circulated by means of a fluid supply device 4 disposed below the incubation bath 3.

A sample disk 5 is disposed in side-by-side relationship to the reaction disk 1 in such a manner as to be rotatable about a vertical axis thereof to support a large number of sample cups 6 on an upper surface thereof. The sample in each of the sample cups 6 is sucked with a probe 7a of a sample pipette 7 and then injected into a predetermined reaction vessel 2.

A reagent disk 8 for supporting a large number of reagent bottles 9 on an upper surface thereof is also disposed in side-by-side relationship to the reaction disk 1 in such a manner as to be rotatable about a vertical axis thereof. The reagent disk 8 is provided with a reagent pipette 10 having a probe 10a which transfers a predetermined amount of reagent from a corresponding bottle 9 into the reaction vessel 2 which has already received a sample. The sample and reagent which have been transferred to the vessel 2 are stirred by stirring means 11 disposed adjacent to the reaction disk 1 in order to accelerate reaction.

The result of the reaction between the sample and reagent is measured by a measuring device provided on the reaction disk 1. The measuring device consists of a multi-wavelength photometer 12 and a light source 13. The reaction vessel 2 accommodating an object for measurement, i.e., reaction product, is placed between the multi-wavelength photometer 12 and the light source 13, so that the result of the reaction which takes place in that reaction vessel 2 is measured by the measuring device. The reaction vessel 2 on which measurement has been completed is cleaned by a cleaning mechanism 14 provided on the reaction disk 1.

The sample pipette 7 is operated by a sample pipetting mechanism 20, while the reagent Pipette 10 is operated by a reagent pipetting mechanism 18. A cleaning water pump 19 supplies cleaning water to the cleaning mechanism 14. The reaction product in the reaction vessel and the water used to clean the reaction vessel 2 are drained from the cleaning mechanism 14 by means of a vacuum pump 59 in the manner described later. The reagent pipetting mechanism 18, the cleaning water pump 19, the vacuum pump 59 and the sample pipetting mechanism 20 are controlled by a computer 15 through an interface 16. The photometer 12 is connected to the interface 16 through an analog/digital converter 17. The interface 16 is connected to a printer 21, to a CRT 22 and to a floppy disk 23.

Although both the sample disk 5 and reagent disk are also provided with cleaning mechanisms similar to the cleaning mechanism 14, illustration thereof is omitted for simplifying the drawings.

The basic operation of the automatic analyzing apparatus having the described structure will be described below. A plurality of cups 6 each of which contains a sample are disposed on the sample disk 5. Rotation of the sample disk 5 is controlled by the computer 15 through the interface 16. As the sample disk 5 has been rotated to a position at which a desired sample cup is located below the sample pipetting probe 7a, the sample in that sample cup 6 is sucked into the probe 7a by means of a pump (not shown) of the sample pipetting mechanism 20 connected to the probe 7a. The probe 7a is then pivoted to inject a predetermined amount of sample into a predetermined reaction vessel 2. The reaction vessel 2 which has received the sample moves to a first reagent adding position in a state where it is held by the reaction disk 1. At the first reagent adding position, a predetermined first reagent, sucked from the reagent bottle 9 on the reagent disk 8 by the reagent dispensing probe 10a operated by the action of a pump (not shown) of the reagent dispensing mechanism 18, is poured into the reaction vessel 2 from the probe 10a. The reaction vessel 2 which has received both the sample and the first reagent moves to a measuring position where rays of light emitted from the light source 13 pass through the vessel 2 and the contents thereof. The optical physical quantity of the contents is detected by the multi-wavelength photometer 12. A signal representing the detected optical physical quantity is converted into a digital signal by the A/D converter 17 and the resultant digital signal is input through the interface 16 into the computer 15 which converts the digital signal into a concentration of a measured object in the measured sample. The data representative of the concentration is input through the interface 16 either into the printer 21 for printing out the result of the measurement or into the CRT 22 which displays the result. The reaction vessel 2 for which measurement has been completed moves to the position of the cleaning mechanism 14 where the sample liquid contained in the reaction vessel 2 is discharged in the manner described later. Then, the reaction vessel 2 is cleaned with the water from the cleaning water pump 19 for reuse for a subsequent analysis.

An operation panel 24 is used to input predetermined commands or data to change the analysis conditions or the like. The floppy disk 23 is used to store the data obtained by the analysis.

Figure 2:
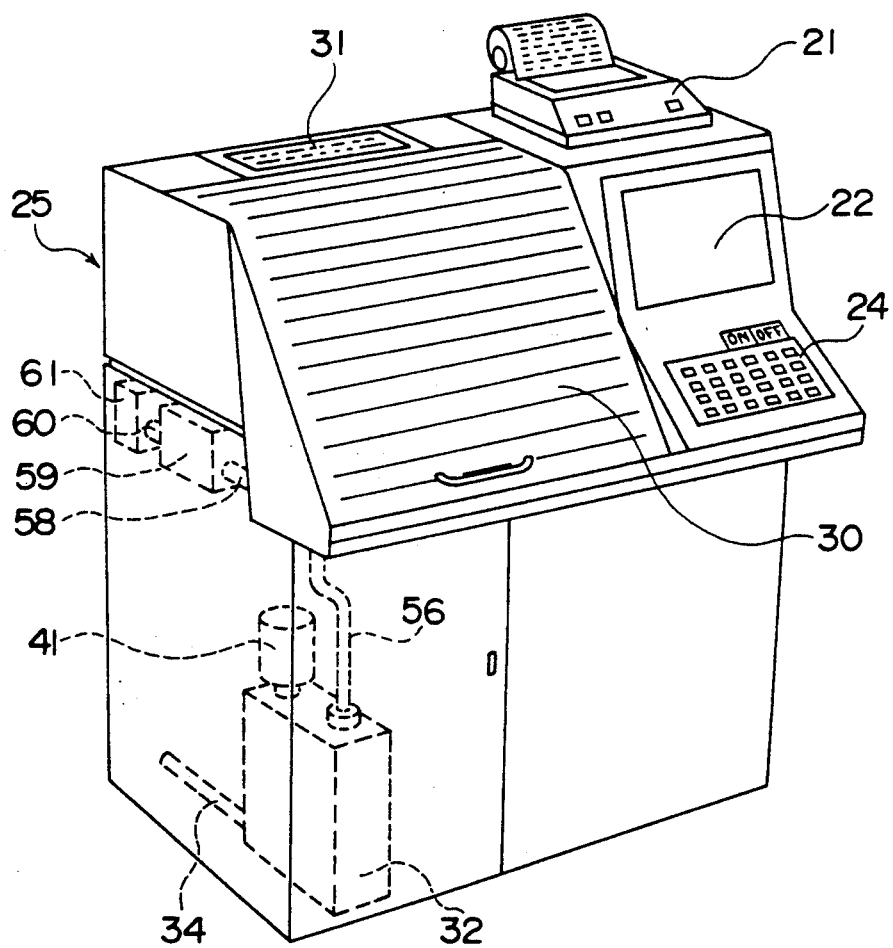
FIG. 2 is a perspective view of the automatic analyzing apparatus of FIG. 1 showing the external appearance thereof.

FIG. 2 shows the outer appearance of the automatic analyzing apparatus. The analyzing portion having the structure shown in FIG. 1 is housed in a housing 25 which can be hermetically sealed by an operable lid member 30 during measurement. The lid member 30 is opened and closed automatically or manually. On the outer surface of the housing 25 are disposed the operation panel 24, the CRT 22 and the printer 21 shown in FIG. 1. An air vent 31 is provided in the top of the housing 25 and above the analyzing portion so as to communicate the space surrounding the analyzing portion in the housing 25 with the atmosphere. A waste reservoir 32 is disposed within the housing 25 below the analyzing portion so as to collect and store therein the waste liquid drained from the reaction vessel 2 via a drainage line 56 in the manner described later.

Figure 3:
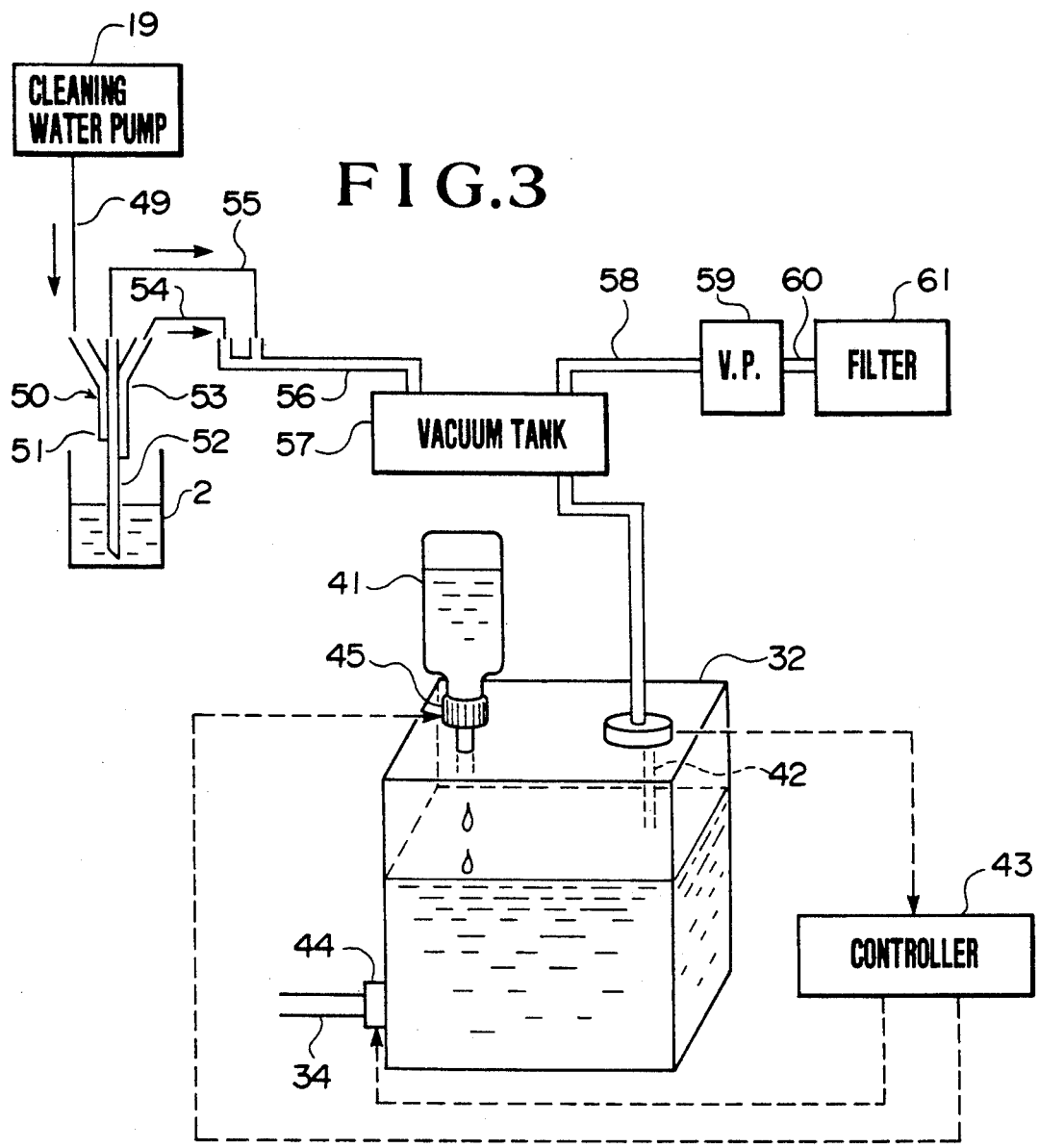
FIG. 3 is a schematic view of drainage line, a filter provided on the drainage line, a waste liquid reservoir and a sterilizing liquid supply device of the automatic analyzing apparatus of FIG. 1.

The cleaning mechanism 14 supports a nozzle assembly 50 consisting of a plurality of nozzles in such a manner that the nozzle assembly 50 can move in a vertical direction (see FIG. 1). When a reaction vessel 2 to be cleaned has come to the cleaning position, the nozzle assembly 50 is moved downward and inserted into the reaction vessel 2. FIG. 3 shows a typical example of the nozzle assembly 50. The nozzle assembly 50 shown in FIG. 3 consists of a cleaning water dispensing nozzle 51 connected to the cleaning water pump 19 via a line 49, a long suction nozzle 52 and a short overflow suction nozzle 53. The nozzles 52 and 53 are connected to an upper end of the drainage line 56 via flexible tubes 55 and 54, respectively. The lower end of the drainage line 56 is detachably connected to the waste liquid reservoir 32. A vacuum tank 57 is provided on the drainage line 56. A vacuum pump 59 is mounted on the top wall of the vacuum tank 57 through a tube 58 so as to communicate with the space in the upper portion of the vacuum tank 57.

Once the nozzle assembly 50 is inserted into a reaction vessel 2, the vacuum pump 59 suckes the reaction solution in the reaction vessel 2 through the nozzle 52. Simultaneously, the cleaning water pump 19 is operated to dispense the cleaning water into the vessel 2 through the nozzle 51 to thereby clean the interior of the reaction vessel 2. At that time, suction force of the vacuum pump 59 also acts on the overflow suction nozzle 53, so that overflow of the cleaning water from the vessel 2 is thus prevented. When cleaning is completed, the operation of the cleaning water pump 19 is stopped and the liquid remaining in the vessel 2 is sucked through the long nozzle 52. The liquid and the suspended particles (infectious aerosol) in the vessel 2, which are sucked through the nozzles 52 and 53, flow into the vacuum tank 57 provided in the drainage line 56. The gas containing the infectious aerosol scattered from the liquid in the tank 57 is discharged from the tank 57 by means of the vacuum pump 59, while the liquid in the tank 57 flows into the waste liquid reversoir 32 by gravity.

The automatic analyzing apparatus having the above-described structure and operated in the manner described above has been known. The improvement according to the present invention will be described below.

Figure 4:
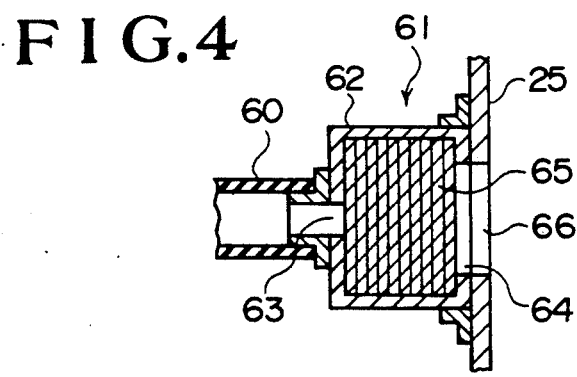
FIG. 4 is a cross-sectional view of the filter of FIG. 3.

As shown in FIGS. 3 and 4, the outlet of the vacuum pump 59 is connected to a filter 61 through a hose 60. The filter 61 includes a box-like casing 62 having an inlet 63 and an outlet 64 and a filtering material 65 replaceably accommodated in the casing 62. The casing 62 is mounted on the inner surface of the rear wall of the housing 25 such that the outlet 64 thereof is aligned with an air outlet 66 formed in the rear wall of the housing 25 of the analyzing apparatus. The filtering material 65 comprises a known HEPA filter (a high efficiency particulate air filter) consisting of a stack of a large number of sheets of filtering paper. The filtering material 65 has an ability of filtering not less than 99.97% of particles (including viruses and bacteria) having a particle size of not less than 0.3 microns. The filtering material 65 is replaced with a new one after use for a predetermined period. For this purpose, one side wall of the casing 62 is openable. The structure of such a casing is apparent to those skilled in the art and thus is not shown.

Turning back to FIG. 3, an electro-magnetic valve 45 is mounted in a hole formed in the top wall of the waste liquid reservoir 32. A sterilizing liquid bottle 41 for containing a sterilizer or a disinfectant, such as aqueous solution of sodium hypochloride, is detachably connected to the valve 45. The waste liquid reservoir 32 has a drainage port 34 which is opened and closed by means of an electro-magnetic valve 44. The operations of the electro-magnetic valves 44 and 45 are controlled by a controller 43 which is electrically connected to the interface 16 shown in FIG. 1. A liquid level detector 42 is provided within the waste liquid reservoir 32. The liquid level detector 42 outputs a level signal to the controller 43 when the surface of the liquid in the waste liquid reservoir 32 reaches a predetermined level (e.g., 80% of the depth of the reservoir 32). Upon receipt of the level signal, the controller 43 sends a signal to the valve 44 to open it and thereby drain the waste liquid from the reservoir 32 through the drainage port 34. When drainage is completed, the controller 43 closes the valve 44.

The electro-magnetic valve 45 is controlled by the controller 43 such that it supplies the sterilizer or the disinfectant into the waste liquid reservoir 32 in the manner described below. When drainage of the waste liquid reservoir 32 is completed and the draining valve 44 is thereby closed, the valve 45 is opened by a signal from the controller 43 to allow a predetermined amount of the sterilizer or the disinfectant in the sterilizing liquid bottle 41 to be poured into the waste liquid reservoir 32. Therefore, the sterilizing liquid in the reservoir 32 makes contact with the waste liquid which will thereafter flow into the waste liquid reservoir 32 for a period of time longer than required for the sterilizing liquid to exhibit its effect.

Also, at the final stage of the cleaning process which is conducted each time analysis is performed, the valve 45 is opened to supply a predetermined amount of the sterilizing liquid into the reservoir 32 regardless of the amount of waste liquid which flows into the waste liquid reservoir 32. Furthermore, the valve 45 is opened to supply a predetermined amount of the sterilizer or the disinfectant into the reservoir 32 whenever a predetermined amount of waste liquid is stored in the waste liquid reservoir 32 during an analysis operation of the analyzing apparatus. Therefore, even when the effect of the batch of the sterilizing liquid supplied immediately after the drainage valve 44 of the waste liquid reservoir 32 has been closed lessens, new batches of sterilizing liquid supplied thereafter at the above-described intervals work effectively as a sterilizer.

In addition to the aforementioned operations, the valve 45 is opened each time when the analyzing apparatus is switched on to supply a predetermined amount of sterilizing liquid into the reservoir 32. Consequently, since a new predetermined amount of sterilizing liquid is supplied into the waste liquid reservoir 32 each time when the apparatus is switched on, the newly added sterilizing liquid exhibits its sterilization effect, even if the effect of the sterilizing liquid previously supplied into the reservoir 32 lessens. These repeated supplies of the sterilizing liquid eliminate any after-sterilization or disinfection process to be conducted on the waste liquid to be discharged out of the apparatus.

As will be understood from the foregoing description, in the automatic analyzing apparatus according to the present invention, since the infectious aerosol discharged from the vacuum pump 59 for sucking waste liquid from the reaction vessels 2 is trapped by the filter before the waste liquid is discharged out of the apparatus, contamination of the space in which the automatic analyzing apparatus according to the present invention is installed can be prevented. Furthermore, the waste liquid which flows into the waste liquid reservoir 32 is sterilized therein sufficiently to assure a safe and simple discarding process.

What is claimed is:

1. An automatic analyzing apparatus for analyzing samples including egesta from organisms and tissues thereof, including:

a housing;

analysis means disposed within said housing, including at least one reaction vessel and a reaction vessel supporting means for supporting said at least one reaction vessel for accommodating a sample and a reagent, and measurement means for measuring the result of the reaction between the sample and the reagent in the reaction vessel;

a waste liquid reservoir detachably disposed within said housing;

cleaning means disposed within said housing for cleaning with cleaning water a reaction vessel which has been used for an analysis;

liquid conveying means disposed within said housing and in fluid communication with said waste liquid reservoir for conveying reaction liquid formed of the sample and the reagent as well as the water used for cleaning the reaction vessel to said waste liquid reservoir; and sterilizing liquid supply means disposed within said housing and in fluid communication with said waste liquid reservoir for supplying a sterilizer or disinfection into said waste liquid reservoir, wherein said liquid conveying means includes at least one suction nozzle movable into and out of the reaction vessel, a drainage line extending from said nozzle to said waste liquid reservoir, gas-liquid separation means provided in said drainage line, a vacuum pump for sucking the gas separated from the liquid within said gas-liquid separation means and containing suspended particles, and a filter for filtering the gas discharged from said vacuum pump and containing an infectious aerosol.

2. The automatic analyzing apparatus according to claim 1, wherein said sterilizing liquid supply means includes a sterilizer or disinfection supply source detachably connected to said waste liquid reservoir, a first valve for controlling communication between said sterilizing liquid supply source and said waste liquid reservoir, and a controller for controlling opening/closing of said first valve, and wherein said waste liquid reservoir includes a level detector for detecting a level of the waste liquid stored in said reservoir and for outputting a signal representing the results of the detection to said controller, and a second valve operable by said controller to discharge the waste liquid from said waste liquid reservoir, said first valve being controlled by said controller such that said first valve opens and thereby allows a predetermined amount of the sterilizing liquid to be poured into said waste liquid reservoir after a discharge of the waste liquid from said waste liquid reservoir is completed and said second valve is thereby closed.

3. The automatic analyzing apparatus according to claim 2, further including electric control means for controlling the operation of said analysis means, said controller being electrically connected to said electric control means, and said first valve being controlled such that said first valve opens to allow a predetermined amount of the sterilizing liquid to be supplied into said waste liquid reservoir at the final stage of the cleaning conducted each time when an analyzing operation of said analyzing apparatus is completed and regardless of the amount of waste liquid which flows into said waste liquid reservoir.

4. The automatic analyzing apparatus according to claim 3, wherein said first valve is controlled such that said first valve further opens to allow a predetermined amount of sterilizing liquid to be supplied into said waste liquid reservoir each time when the waste liquid in said waste liquid reservoir reaches a predetermined level during an analysis operation of said analyzing apparatus.

5. The automatic analyzing apparatus according to claim 4, wherein said first valve is controlled such that said first valve opens to allow a predetermined amount of the sterilizing liquid to be supplied into said waste liquid reservoir each time when said analyzing apparatus is switched on.

6. An automatic analyzing apparatus for analyzing samples including egesta from organisms and tissues thereof, including:

a housing;

analysis means disposed within said housing, including at least one reaction vessel and a reaction vessel supporting means for supporting said at least one reaction vessel for accommodating a sample and a reagent, and measurement means for measuring the result of the reaction between the sample and the reagent in the reaction vessel;

a waste liquid reservoir detachably disposed within said housing;

cleaning means disposed within said housing for cleaning with cleaning water the reaction vessel which has been used for an analysis;

liquid conveying means disposed within said housing and in fluid communication with said cleaning means for conveying reaction liquid formed of the sample and the reagent as well as the water used for cleaning the reaction vessel to said waste liquid reservoir; and sterilizing liquid supply means disposed within said housing and in fluid communication with said waste liquid reservoir for supplying a sterilizer or disinfectant into said waste liquid reservoir, wherein said sterilizing liquid supply means includes a sterilizing liquid supply source detachably connected to said waste liquid reservoir, a first valve for controlling communication between said sterilizing liquid supply source and said waste liquid reservoir, and a controller for controlling opening/closing of said first valve, and wherein said waste liquid reservoir includes a level detector for detecting a level of the waste liquid stored in said reservoir and for outputting a signal representing the results of the detection to said controller, and a second valve openable by said controller to discharge the waste liquid from said waste liquid reservoir, said first valve being controlled by said controller such that said first valve opens to allow a predetermined amount of the sterilizing liquid to be supplied into said waste liquid reservoir after a discharge of the waste liquid from said waste liquid reservoir is completed and said second valve is thereby closed.

7. The automatic analyzing apparatus according to claim 6, further including electric control means for controlling the operation of said analysis means, said controller being electrically connected to said electric control means, and said first valve being controlled such that said first valve opens to allow a predetermined amount of the sterilizing liquid to be supplied into said waste liquid reservoir at the final stage of the cleaning which is conducted each time when an analyzing operation of said analyzing apparatus is completed and regardless of the amount of waste liquid which flows into said waste liquid reservoir.

8. The automatic analyzing apparatus according to claim 7, wherein said first valve is controlled such that said first valve opens to allow a predetermined amount of the sterilizing liquid to be supplied into said waste liquid reservoir each time when the waste liquid in asid waste liquid reservoir reaches a predetermined level during an analysis operation of said analyzing apparatus.

9. The automatic analyzing apparatus according to claim 8, wherein said first valve is controlled such that said first valve opens to allow a predetermined amount of the sterilizing liquid to be supplied into said waste liquid reservoir each time when said analyzing apparatus is switched on.

10. An automatic analyzing apparatus for analyzing samples including egesta from organisms and tissues thereof, comprising:

a housing;

analysis means disposed within said housing, including a reaction vessel supporting means for supporting said at least one reaction vessel for accommodating a sample and a reagent, and measurement means for measuring the result of the reaction between the sample and the reagent in the reaction vessel;

a waste liquid reservoir detachably disposed within said housing;

cleaning means disposed within said housing for cleaning with cleaning water a reaction vessel which has been used for an analysis; and liquid conveying means disposed within said housing and in fluid communication with said cleaning means for conveying reaction liquid formed of the sample and the reagent as well as the water used for cleaning the reaction vessel to said waste liquid reservoir;

wherein said liquid conveying means includes at least one suction nozzle movable into and out of the reaction vessel, a drainage line extending from said nozzle to said waste liquid reservoir, gas-liquid separation means provided in said drainage line, a vacuum pump for sucking the gas separated from the liquid within said gas-liquid separation means and containing suspended particles, and a filter for filtering the gas discharged from said vacuum pump and containing an infectious aerosol.

* * * * *